United States Patent
Young et al.

(10) Patent No.: US 9,358,030 B2
(45) Date of Patent: Jun. 7, 2016

(54) ULTRASONIC SURGICAL TOOL

(75) Inventors: Michael John Radley Young, South Devon (GB); Stephen Michael Radley Young, South Devon (GB)

(73) Assignee: SRA DEVELOPMENTS LIMITED, South Devon (GB)

(*) Notice: Subject to any disclaimer, the term of this patent is extended or adjusted under 35 U.S.C. 154(b) by 1128 days.

(21) Appl. No.: 12/441,910

(22) PCT Filed: Sep. 18, 2007

(86) PCT No.: PCT/GB2007/003560
§ 371 (c)(1),
(2), (4) Date: Oct. 13, 2009

(87) PCT Pub. No.: WO2008/065323
PCT Pub. Date: Jun. 5, 2008

(65) Prior Publication Data
US 2012/0010537 A1    Jan. 12, 2012

(30) Foreign Application Priority Data

Sep. 19, 2006 (GB) .................................. 0618366.9
Mar. 13, 2007 (GB) .................................. 0704823.4

(51) Int. Cl.
*A61B 17/32* (2006.01)
*A61B 17/22* (2006.01)

(52) U.S. Cl.
CPC .............. *A61B 17/320068* (2013.01); *A61B 2017/22008* (2013.01); *A61B 2017/320076* (2013.01)

(58) Field of Classification Search
CPC ........... A61B 17/320068; A61B 2017/320072; A61B 2017/22015; A61B 2017/320096; A61B 17/22004; A61B 2017/22014; A61C 3/03; A61F 9/00745

USPC ................................ 606/39, 41, 45, 170, 171
See application file for complete search history.

(56) References Cited

U.S. PATENT DOCUMENTS

| 2,528,941 A | 11/1950 | Bassett et al. |
| 2,990,616 A * | 7/1961 | Kuris et al. .................. 433/119 |
| 3,565,062 A | 2/1971 | Kuris |
| 3,657,056 A | 4/1972 | Garvey et al. |
| 3,792,701 A | 2/1974 | Kloz et al. |
| 3,861,391 A | 1/1975 | Antonevich et al. |

(Continued)

FOREIGN PATENT DOCUMENTS

| CN | 1745721 A | 3/2006 |
| EP | 0 619 993 A1 | 10/1994 |

(Continued)

OTHER PUBLICATIONS

PCT International Preliminary Report on Patentability for PCT/GB2007/003560 filed Sep. 18, 2007, dated Mar. 24, 2009.

(Continued)

*Primary Examiner* — Sarah W Aleman
(74) *Attorney, Agent, or Firm* — Heslin Rothenberg Farley & Mesiti P.C.

(57) ABSTRACT

The shaped output is for use with an ultrasonic surgical tool vibratable in torsional mode. The output has a generally cylindrical first waveguide (1) with, at a distal end a second waveguide extension member (3) of reduced diameter. The second waveguide (3) is curved in one plane from the axis of the first waveguide. It has at least two blade faces (4) extending radially outwardly from its distal end.

19 Claims, 3 Drawing Sheets

(56) References Cited

U.S. PATENT DOCUMENTS

Figure 1:
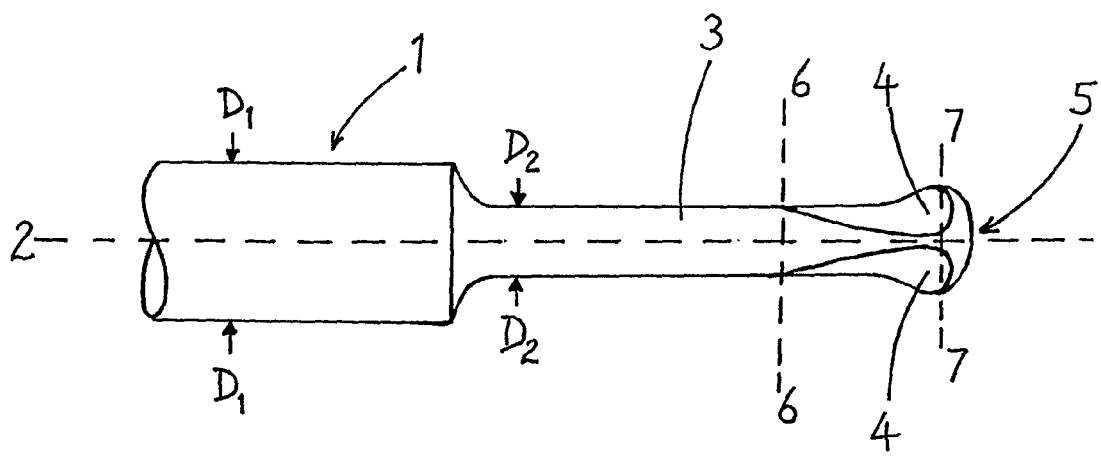

| | | | |
|---|---|---|---|
| 4,144,646 A | 3/1979 | Takemoto et al. | |
| 4,188,952 A | 2/1980 | Loschilov et al. | |
| 4,248,232 A | 2/1981 | Engelbrecht et al. | |
| 5,019,083 A | 5/1991 | Klapper et al. | |
| 5,151,099 A | 9/1992 | Young et al. | |
| 5,167,619 A | 12/1992 | Wuchinich | |
| 5,188,102 A * | 2/1993 | Idemoto et al. | 604/22 |
| 5,322,055 A | 6/1994 | Davison et al. | |
| 5,324,297 A | 6/1994 | Hood et al. | |
| 5,324,299 A | 6/1994 | Davison et al. | |
| 5,330,481 A | 7/1994 | Hood et al. | |
| 5,413,107 A | 5/1995 | Oakley et al. | |
| 5,520,678 A | 5/1996 | Heckele et al. | |
| 5,549,544 A | 8/1996 | Young et al. | |
| 5,656,015 A | 8/1997 | Young | |
| 5,695,510 A | 12/1997 | Hood | |
| 5,749,877 A | 5/1998 | Young | |
| 5,873,873 A | 2/1999 | Smith et al. | |
| 5,885,301 A | 3/1999 | Young | |
| 5,935,143 A | 8/1999 | Hood et al. | |
| 6,004,335 A | 12/1999 | Vaitekunas et al. | |
| 6,056,735 A | 5/2000 | Okada et al. | |
| 6,129,735 A | 10/2000 | Okada et al. | |
| 6,254,623 B1 * | 7/2001 | Haibel et al. | 606/169 |
| 6,425,906 B1 | 7/2002 | Young et al. | |
| 6,971,994 B1 | 12/2005 | Young et al. | |
| 8,512,340 B2 * | 8/2013 | Easley et al. | 606/79 |
| 2002/0099400 A1 | 7/2002 | Wolf et al. | |
| 2004/0044356 A1 | 3/2004 | Young et al. | |
| 2005/0021065 A1 | 1/2005 | Yamada et al. | |
| 2005/0177184 A1 | 8/2005 | Easley | |

FOREIGN PATENT DOCUMENTS

| | | | |
|---|---|---|---|
| EP | 0 646 435 A1 | 4/1995 | |
| EP | 0 970 659 A | 1/2000 | |
| EP | 0 970 660 | 1/2000 | |
| EP | 0970660 A1 | 1/2000 | |
| EP | 1 138 264 | 10/2001 | |
| EP | 1138264 A1 | 10/2001 | |
| EP | 1 229 515 A2 | 8/2002 | |
| EP | 1 625 836 | 2/2006 | |
| EP | 1 693 027 A | 8/2006 | |
| GB | 2333709 | 8/1999 | |
| GB | 2 365 775 A | 2/2002 | |
| GB | 2 423 931 | 9/2006 | |
| GB | 2425480 A | 11/2006 | |
| SU | 1388002 | 4/1988 | |
| SU | 1388002 A1 | 4/1988 | |
| WO | WO 99/35982 | 7/1999 | |
| WO | WO 99/52489 | 10/1999 | |
| WO | WO 01/21079 A1 | 3/2001 | |
| WO | WO 02/38057 | 5/2002 | |
| WO | WO 03/047769 | 6/2003 | |
| WO | WO 03/082132 A1 | 10/2003 | |
| WO | WO 03082133 | 10/2003 | |
| WO | WO 2005/084553 | 9/2005 | |
| WO | WO 2006/008502 | 1/2006 | |
| WO | WO 2006/059120 A | 6/2006 | |
| WO | WO 2006/092576 | 9/2006 | |
| WO | WO2006092327 * | 9/2006 | A61B 17/16 |
| WO | WO 2007/138295 | 12/2007 | |
| WO | WO 2008/065323 | 6/2008 | |

OTHER PUBLICATIONS

PCT Written Opinion of the International Searching Authority for Appln. No. PCT/GB2007/001968 filed May 25, 2007, European Patent Office.

PCT International Search Report dated Sep. 12, 2007 for Appln. No. PCT/GB2007/001968 filed May 25, 2007.

PCT International Preliminary Report on Patentability for PCT/GB2006/000697 filed Feb. 28, 2006, dated Sep. 11, 2007.

International Search Report for PCT/GB2006/000697 dated May 3, 2006.

GB Search Report dated Jun. 27, 2006 for GB0504321.1.

PCT International Search Report for PCT/GB2007/003560 filed Sep. 18, 2007, dated Jan. 3, 2008.

GB Search Report for GB 0718476.5 dated Nov. 29, 2007.

* cited by examiner

ULTRASONIC SURGICAL TOOL

The present invention relates to an improved waveguide output for torsionally vibratable ultrasonic surgical tools, particularly but not exclusively, such as are known from British Patent number 2333709B.

The above patent describes a surgical tool comprising means to generate ultrasonic torsional mode vibrations, a waveguide operatively connected at a proximal end to the generating means and extending a distance therefrom of $n\lambda_T/2$ (where $\lambda_T$ is the wavelength of ultrasonic vibration in the material of the waveguide) to a distal end provided with an output.

Surgical tools having outputs purely for cutting purposes have been described in our British Patent No. 2365775B. However, these are not always easy to use and are not adapted to carry out welding and/or ablation procedures.

It has now been found that further improvements in the configurations of the output of such tools may be made.

It is an object of the present invention to provide an improved waveguide output for such a tool.

According to a first aspect of the present invention there is provided an output means for use with an ultrasonic surgical tool vibratable in torsional mode, said output comprising a generally cylindrical first waveguide provided at a distal end with a second waveguide extension member of reduced diameter, and being curved in one plane from the axis of the first waveguide, and at least two blade means extending radially from a distal end of the second waveguide extension member.

Preferably the output means is provided with two blade means extending radially substantially diametrically opposite one from the other.

Advantageously the blade means extend in a plane substantially orthogonal to the plane of curvature of the waveguide extension member.

The distal end of the extension member may be rounded, with the blade means actionable retroactively.

The diameter of the extension member may be no more than half the diameter of the first waveguide.

The curvature of the waveguide extension member may be such that the distal end thereof and the blade means carried thereby do not extend from the axis of the first waveguide beyond a distance equal to the radius of the first waveguide.

According to a second aspect of the present invention, there is provided a surgical tool comprising means to generate torsional mode ultrasonic vibrations, and a waveguide output as described above operatively connected thereto.

Figure 2:
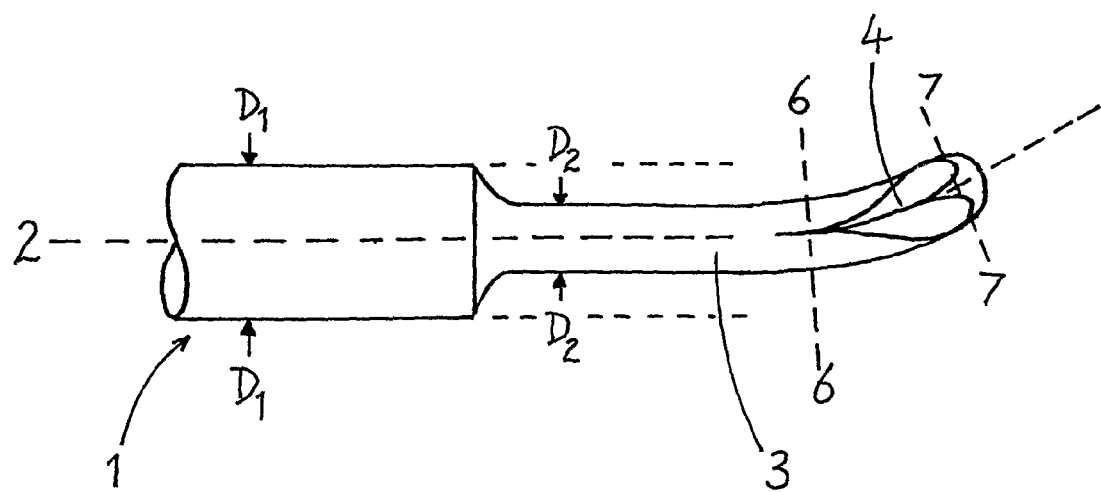
Figure 3A:
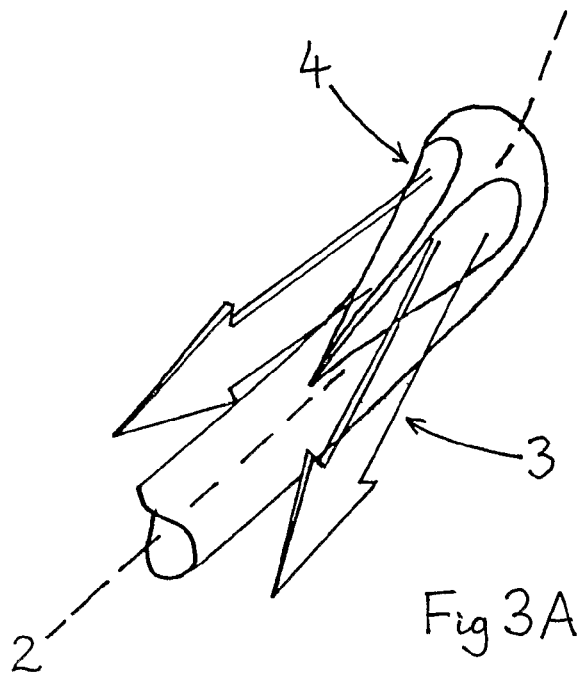
Figure 3B:
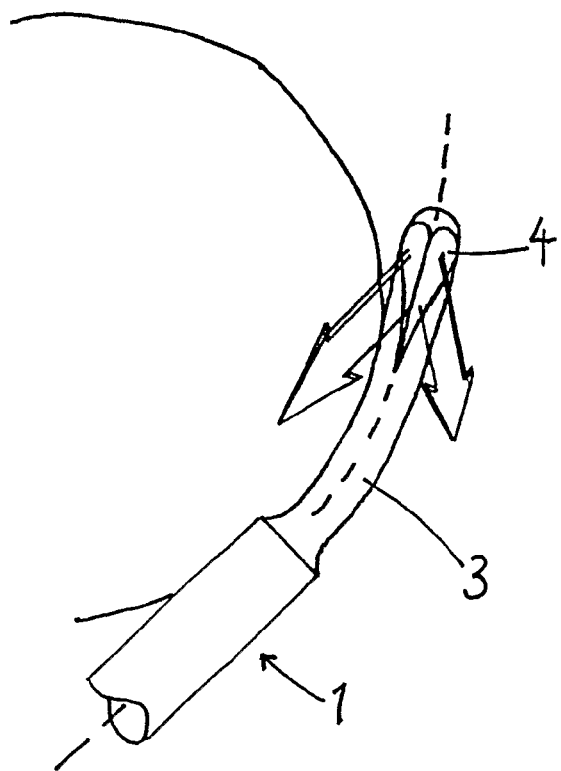
Figure 3C:
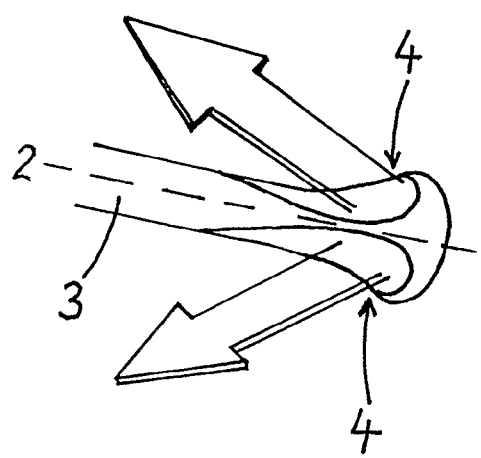
Figure 4:
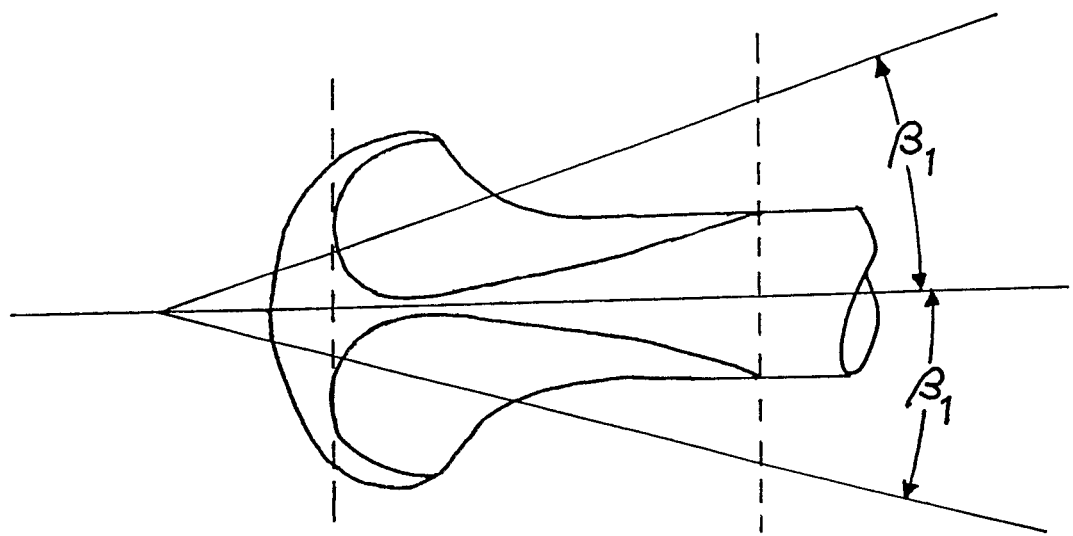
Figure 5:
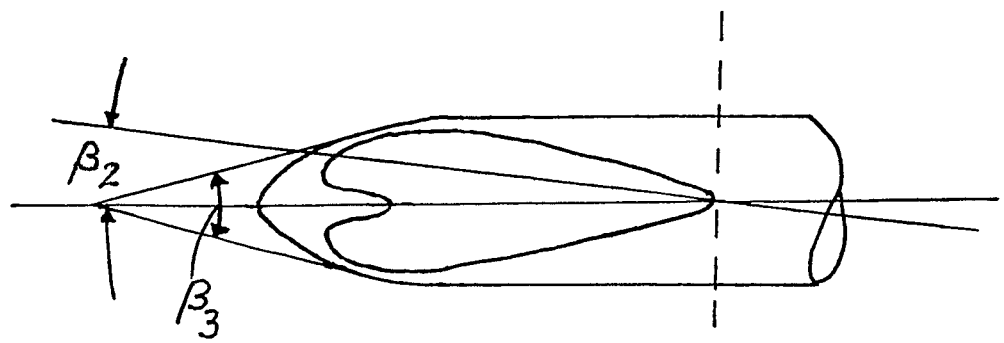

An embodiment of the present invention will now be more particularly described by way of example and with reference to the accompanying drawings, in which:

FIG. 1 is a view from above of an output;
FIG. 2 is a side elevation of the output;
FIG. 3a is a view from above of an output;
FIG. 3b is a side elevation of the output;
FIG. 3c is a detail to show the directional nature of the energy generated;
FIG. 4 is a view from above showing the distal end of the output; and
FIG. 5 is a side view of the distal end of the output.

A torsional mode vibration provides concentric motion about the axis of the waveguide. Sections of the blade non-parallel with the motion provide vibrating faces capable of imparting energy directly into tissue brought to bear on such a face rather than cause friction as in conventional, parallel motion devices.

The greater the distance of a point from the longitudinal axis, the greater will be the amplitude of the vibration.

Referring now to the drawings, FIG. 1 is a view from above and FIG. 2 is a side elevation of an output at a distal end of a waveguide 1, torsionally vibratable about its longitudinal axis 2.

The waveguide 1 extends longitudinally in a distal direction by means of integral extension 3. This extension has a diameter $D_2$ which is at most half the diameter of the initial output $D_1$.

The extension 3 is curved adjacent its distal end in one plane so that active surfaces at its distal end extend from axis 2 no further than a projection of the initial output diameter $D_1$.

A pair of oppositely directed blades 4 projects radially outwardly at a distal end from this generally cylindrical waveguide extension 3 and are able to generate high angular vibrational displacements. The waveguide extension 3 and the blades 4 are machined at their distal end to have a smoothly rounded nose 5 which continues around to the outer edges of the blades 4.

FIG. 2 shows a side elevation of the curvedly shaped output extension 3. The curvature is in one plane substantially orthogonal to the general plane of the radially extending blades 4. The extent of the curvature is such that the active edges of the blade 4 do not extend beyond a projection of the diameter $D_1$ of the initial output 1. The diameter $D_2$ of the output extension 3 is such that $D_1 \geq 2 D_2$.

As can be seen from FIG. 3 the head has four pockets of generally cylindrical profile cut into it, each of which is so shaped as to generate, under torsional ultrasonic vibrational mode, a focussed compression wave into the surrounding tissue, most particularly that being cut.

Such a compression wave and its associated cavitation effects creates a local heating which aids in haemostasis at the moment of cutting.

Use of the output offers several critical features.

Firstly there is a high rotational displacement at the blades 4 radially distant from the axis of vibration about axis 2, giving vibrations of increased amplitude. The greater the distance of a point from the longitudinal axis, the greater will be the amplitude of the vibration.

The rotational movement from plane 6 to plane 7 increases in proportion to increase in diameter; the displacement gradient created in this area results in contacting material being drawn from the distal region; associated with high amplitude and high energy to the lower amplitude low energy exit plane 6, thus creating a focusing effect. The highly directional cavitation field, with associated heating, is directed as shown in FIG. 3.

Secondly, the oppositely facing blades 4 enable the tool to be used in either direction without the need for the surgeon to manipulate the tool excessively. The blades 4 are so formed to allow use by retro-action of the waveguide for cutting tissue by pulling the tool backwardly, having engaged the tissue in close proximity with the cutting edge, as might be customary with a conventional unpowered scalpel.

The curved shape of the output extension 3 is more ergonomic, especially when used with some tissue planes.

Thirdly, focussed energy permits the active head to be guided by the surgeon to create effective haemostasis in targeted tissue sites. Curvature of the output section in the plane of the radially extended lobes permits access to curved structures such as a femoral head with associated joint capsule (as indicated in FIG. 3b).

The thickness of the web formed between the blades 4 and main axial body 3 of the waveguide represents a region of maximum displacement due to its cross section variation, having a minimum thickness along the cutting edges, and greater thicknesses towards the generally cylindrical waveguide extension 3.

Welding and/or ablation of tissue or blood vessels may be achieved by turning the tool and/or pressing the transverse face of a radially extending blade 4 onto the target tissue, so subjecting it to high amplitude compression waves.

The rotational movement from plane 6 to plane 7 increases in proportion to increase in diameter of the head. The displacement gradient created in this area results in contacting material being drawn from the distal region, associated with high amplitude and high energy to the lower amplitude low energy exit plane 6, thus creating a focusing effect. The highly directional cavitation field, with associated heating, is directed as shown in FIG. 3, with much improved results in terms of haemostasis during cutting.

As can be seen from FIGS. 4 and 5, the arcuate surface forming the cutting blade is the line of intersection between two cylindrically machined surfaces. These have been created by the movement of a spherical headed machining tool along axes inclined at $\beta_1$ and $\beta_2$ to the longitudinal axis in the orthogonal planes of blade symmetry. When the distal end of the tool is shaped correctly, the waveguide can be bent, preferably in two stages, so that the tool surface can be applied to tissue at a most advantageous aspect.

The invention claimed is:

1. An output means for use with an ultrasonic surgical tool vibratable in torsional mode, said output means comprising:
    a generally cylindrical first waveguide extending along a longitudinal axis and provided at a distal end with a generally cylindrical second waveguide extension member being curved in one plane from the longitudinal axis of the first waveguide,
    a diameter of the second waveguide extension member being less than a diameter of the first waveguide, and
    two blades extending radially from a distal end of the second waveguide extension member, wherein said two blades each comprise two pockets of part-cylindrical profile shaped so as to create, under torsional ultrasonic vibrational mode, a focussed compression wave into surrounding tissue,
    said two pockets are so disposed as to define a cutting edge of a respective blade where said two pockets meet of a respective blade where said two pockets meet,
    said cutting edge of each blade curves outwardly from a central longitudinal axis of the second waveguide extension member and is oriented away from the distal end of the second waveguide extension member so as to cut tissue when the output means is pulled backwardly, and the blades extend in a plane substantially orthogonal to the plane of curvature of the second waveguide extension member.

2. The output means as claimed in claim 1, wherein the output means is provided with said two blades extending radially substantially diametrically opposite one from the other.

3. The output means as claimed in claim 1, wherein the distal end of the second waveguide extension member is rounded, with the cutting edge of each blade aligned away from said distal end of the second waveguide extension member.

4. The output means as claimed in claim 1, wherein the diameter of the second waveguide extension member is no more than half the diameter of the first waveguide.

5. The output means as claimed in claim 1, wherein curvature of the second waveguide extension member is such that the distal end of the second waveguide extension member and the blades carried thereby do not extend from the axis of the first waveguide beyond a distance equal to a radius of the first waveguide.

6. A surgical tool comprising means to generate torsional mode ultrasonic vibrations, and the output means as claimed in claim 1.

7. The output means as claimed in claim 1, wherein said output means is in operative connection with a torsional mode ultrasonic vibration generator at a proximal end of the first waveguide.

8. The output means as claimed in claim 1, wherein said two pockets of part-cylindrical profile of each said blade are each aligned at an angle to the central longitudinal axis of the second waveguide extension member and at an angle to the other of said two pockets of part-cylindrical profile of the respective blade.

9. An output means for use with an ultrasonic surgical tool vibratable in torsional mode, said output means comprising:
    a first portion extending along a longitudinal axis and having a constant cross sectional area, provided at a distal end with a second portion having a constant cross sectional area smaller than the constant cross sectional area of the first portion,
    said second portion carrying blades at or towards a distal end of the second portion and extending from opposite sides of the second portion,
    wherein said second portion is curved towards its distal end such that the distal end of the second portion and the blades carried by the second portion do not extend from the longitudinal axis of the first portion beyond a distance equal to a radius of the first portion, and
    each blade has a cutting edge that curves outwardly from a central longitudinal axis of the second waveguide extension member and is oriented away from the distal end of the second waveguide extension member so as to cut tissue when the output means is pulled backwardly.

10. The output means according to claim 9, wherein said blades each comprise a pair of substantially identical part cylindrical surfaces, which define a cutting edge of the respective blade between said pair.

11. The output means according to claim 9, wherein said blades extend in a plane substantially orthogonal to a plane of curvature of said second portion.

12. The output means according to claim 9, wherein a diameter of the first portion is greater than or equal to two times a diameter of the second portion.

13. The output means according to claim 9, wherein the distal end of said second portion is rounded, with a cutting edge of each blade being aligned away from said distal end of said second portion.

14. An output means for use with an ultrasonic surgical tool vibratable in torsional mode, said output means comprising:
    a first portion having a constant cross sectional area provided at a distal end with a second portion having a constant cross sectional area smaller than the constant cross sectional area of the first portion,
    said second portion comprising blades at or towards a distal end of the second portion and extending from the second portion,
    wherein each of said blades comprises two pockets of part-cylindrical profile shaped so as to create, under torsional ultrasonic vibrational mode, a focused compression wave into a surrounding tissue,
    said pockets define a cutting edge of a respective blade where the two pockets meet,
    said cutting edge of each blade curves outwardly from a central longitudinal axis of the second waveguide extension member and is oriented away from the distal end of the second waveguide extension member so as to cut tissue when the output means is pulled backwardly; and said blades extend in a plane substantially orthogonal to a plane of curvature of said second portion.

15. The output means according to claim 14, wherein said second portion is curved at or towards the distal end of the second portion.

16. The output means according to claim 14, wherein a diameter of the first portion is greater than or equal to two times a diameter of the second portion.

17. The output means according to claim 14, wherein the distal end of said second portion is rounded, with the cutting edge of each blade being aligned away from said distal end of said second portion.

18. The output means as claimed in claim 14, where said two pockets of part-cylindrical profile of each said blade are each aligned at an angle to the central longitudinal axis of the second waveguide extension member and at an angle to the other of said two pockets of part-cylindrical profile of the respective blade.

19. An output means for use with an ultrasonic surgical tool vibratable in torsional mode, said output means comprising:
a first portion extending along a longitudinal axis and having a constant cross sectional area provided at a distal end with a second portion having a constant cross sectional area smaller than the constant cross sectional area of the first portion,
said second portion comprising blades at or towards a distal end of the second portion,
wherein the blades extend in different directions and
wherein said second portion is curved towards the distal end of the second portion such that the distal end of the second portion and the blades carried by the second portion do not extend from the longitudinal axis of the first portion beyond a distance equal to a radius of the first portion, and
each blade has a cutting edge that curves outwardly from a central longitudinal axis of the second waveguide extension member and is oriented away from the distal end of the second waveguide extension member so as to cut tissue when the output means is pulled backwardly.

\* \* \* \* \*